(12) United States Patent
Inoue

(10) Patent No.: US 7,474,774 B2
(45) Date of Patent: Jan. 6, 2009

(54) RADIOGRAPHIC IMAGE PROCESSING METHOD AND APPARATUS, AND GRID SORTING METHOD AND APPARATUS

(75) Inventor: Hitoshi Inoue, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 923 days.

(21) Appl. No.: 10/911,306

(22) Filed: Aug. 4, 2004

(65) Prior Publication Data
US 2005/0031182 A1 Feb. 10, 2005

(30) Foreign Application Priority Data
Aug. 7, 2003 (JP) ............... 2003-289157

(51) Int. Cl.
*G06K 9/00* (2006.01)
(52) U.S. Cl. .................. 382/128; 382/132; 382/131
(58) Field of Classification Search .............. None
See application file for complete search history.

(56) References Cited

U.S. PATENT DOCUMENTS

| 6,614,044 | B2 | 9/2003 | Yamada |
| 6,826,256 | B2 | 11/2004 | Inoue |
| 6,868,137 | B2 | 3/2005 | Inoue |
| 7,142,705 | B2 | 11/2006 | Inoue et al. |
| 2002/0196901 | A1 * | 12/2002 | Inoue .................. 378/154 |
| 2007/0019847 | A1 | 1/2007 | Inoue |

FOREIGN PATENT DOCUMENTS

| JP | 2001-189866 | 7/2001 |
| JP | 2002-152467 | 5/2002 |
| JP | 2002-330344 | 11/2002 |
| JP | 2003-038481 | 2/2003 |

OTHER PUBLICATIONS

Japanese Office Action dated Sep. 8, 2006.

* cited by examiner

*Primary Examiner*—Matthew C Bella
*Assistant Examiner*—Claire Wang
(74) *Attorney, Agent, or Firm*—Morgan & Finnegan LLP

(57) ABSTRACT

A fundamental frequency and at least one harmonic frequency of gridlines in a radiographic image are measured to form a filter for extracting the measured fundamental frequency component and harmonic frequency component. Filtering is performed on the radiographic image using the formed filter. Based on the obtained image data, a gridline model which takes the measured fundamental frequency and harmonic frequency into consideration is fitted to generate a grid image. The gridlines are removed from the radiographic image by the generated grid image.

17 Claims, 16 Drawing Sheets

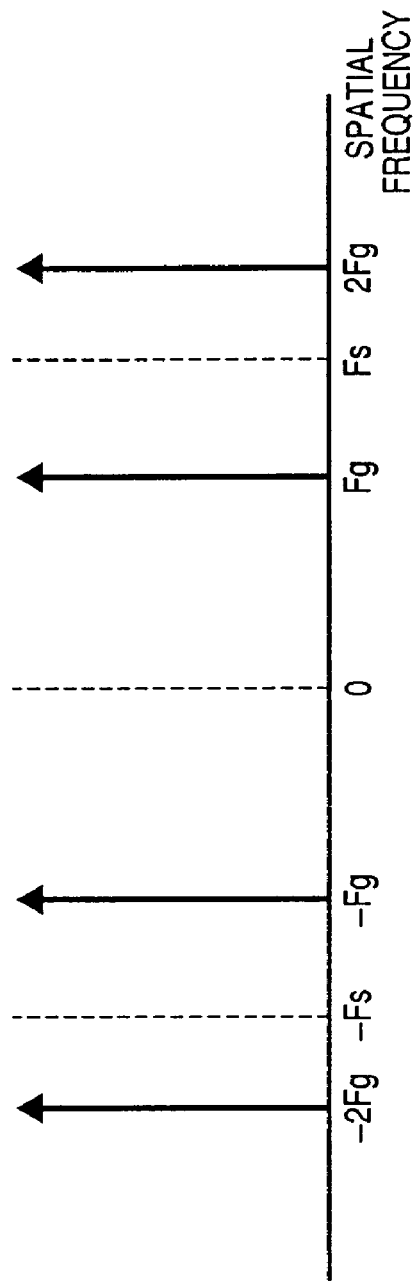
F I G. 12A
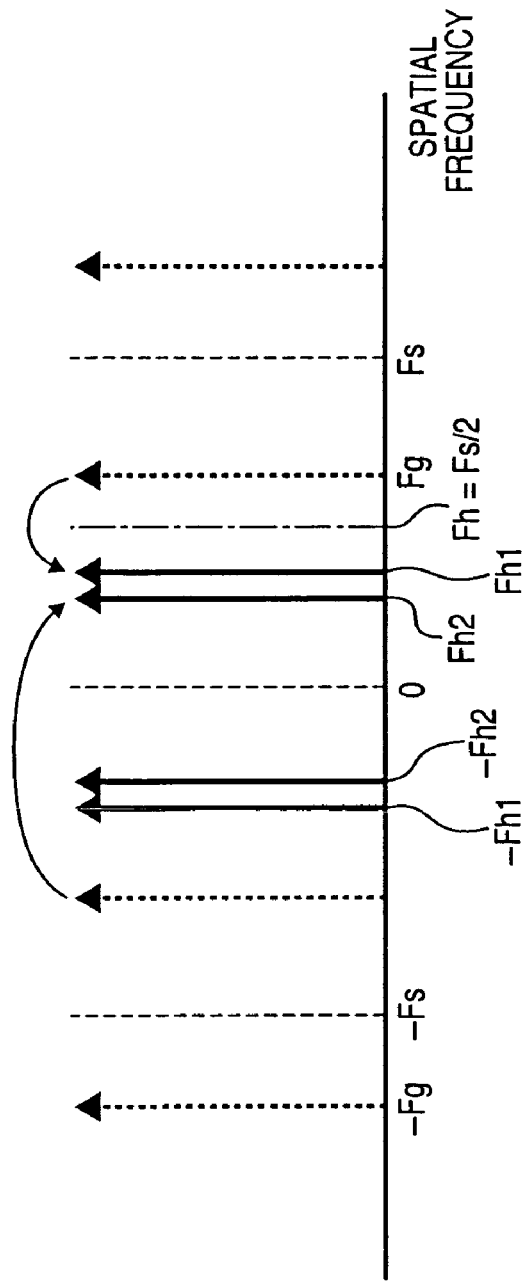
F I G. 12B

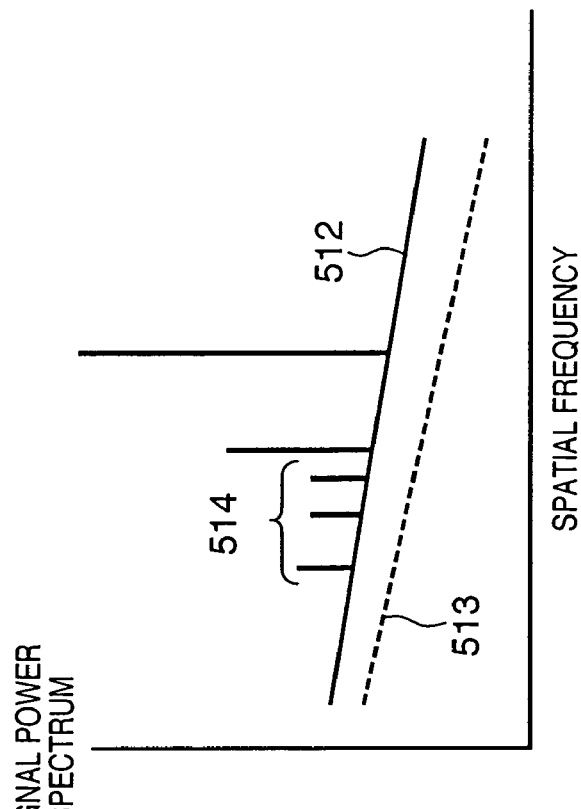
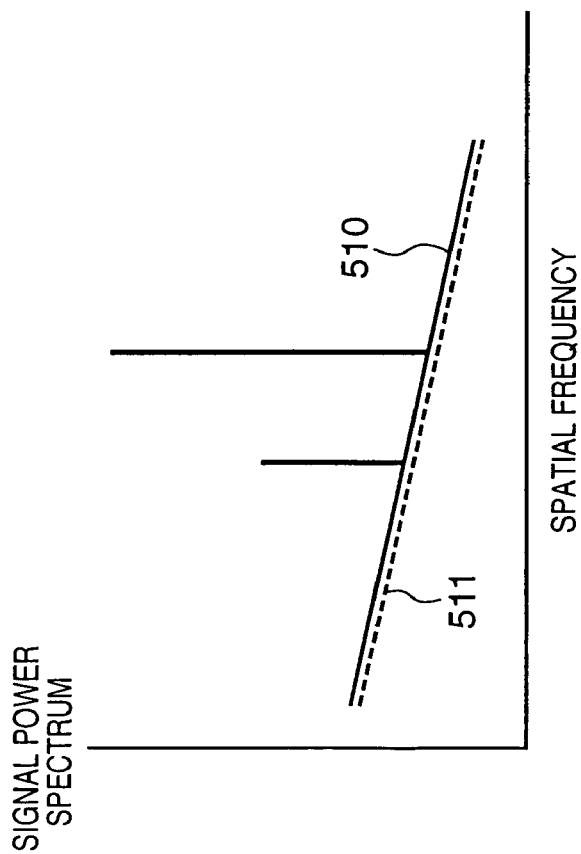

$$\bar{P}_i = \frac{1}{m} \sum_{j=1}^{m} P_{i,j} \quad \cdots (A)$$

$$v_i = \frac{1}{m} \sum_{j=1}^{m} \left( \bar{P}_i - P_{i,j} \right)^2 \quad \cdots (B)$$

$$Vh = \frac{1}{n} \sum_{i=1}^{n} v_i \quad \cdots (C)$$

$$Vs = \frac{1}{n} \sum_{i=1}^{n} \left( \bar{P}_i - G(x_i) \right)^2 \quad \cdots (D)$$

RADIOGRAPHIC IMAGE PROCESSING METHOD AND APPARATUS, AND GRID SORTING METHOD AND APPARATUS

FIELD OF THE INVENTION

The present invention relates to processing of a radiographic image obtained by a radiographic apparatus incorporating an anti-scatter grid. In particular, the invention relates to an image processing technique suitable to processing a medical-use X-ray image.

BACKGROUND OF THE INVENTION

A radiographic image is an image of a spatial intensity distribution of a radiation ray, i.e., an image of a transmittance distribution of a radiation ray, which has transmitted through an object or a human body serving as an object of shooting. A parameter that causes a problem in a case of observing such radiographic image includes an existence of scattered radiation emitted by an object of shooting. In general, a radiographic image is generated using a radiation intensity at an arbitrary position of an image reception surface, which is obtained when an object of shooting lies between the radiation source and image reception surface, as an attenuation factor of the radiation ray on the straight line connecting the arbitrary position and the radiation source. In other words, because a radiation transmittance is obtained for the part of the object that includes the straight line, internal data of a local portion of the object can be obtained on a plane. This is called a direct radiation component.

However, a radiation ray that reaches the image reception surface includes, besides the direct radiation component, a scattered radiation component which is secondarily emitted by the object of shooting itself. Therefore, the radiation intensity is a sum of the direct radiation component and the scattered radiation component. Generally the radiation intensity is expressed by the number of energy particles reaching at random. Therefore, it is known that the radiation intensity obtained on the image reception surface naturally has a Poisson distribution, and that the dispersion (scatter value) is equal to the number of energy particles. Such dispersion causes random noise on the image reception surface. This is equivalent to an addition of scattered radiation that adds noise irrelevant to the shooting object data to the image data obtained on the image reception surface. Since the addition of scattered radiation is equivalent to an addition of random noise, contrast data of an extremely small object of shooting that is buried in the noise may completely be lost. In such case, it is extremely difficult to remove only the scattered radiation component from the image having the scattered radiation by calculation (image processing). As matters stand, it is considered almost impossible.

Since the outset of the X-ray discovery, the use of an anti-scatter grid is available as means for effectively removing the scattered radiation. FIG. 10 is an explanatory view on how to use the anti-scatter grid. Numeral 501 denotes an image reception surface; 502, an anti-scatter grid (hereinafter referred to as the grid); and 503, an object of shooting. The grid 502 is configured with a plurality of lead strips arranged toward the direction of an X-ray source 504 (X-ray focal point). While the direct radiation component from the X-ray focal point passes through the space between the strips and reaches the image reception surface as indicated by dashed lines 505, since the lead strips have a high X-ray blocking rate, the scattered radiation component having an orientation different from that of the direct radiation component is blocked by the strips as indicated by the arrow 506 and does not reach the image reception surface. By this method, a fair amount of the scattered radiation component can be removed. Although a part of the direct radiation component is sacrificed, it is possible to obtain a high-contrast image having little influence of the scattered radiation.

An adverse effect of the grid 502 is that a striped pattern (hereinafter referred to as gridlines), which is a shadow image of the strips, appears on the image reception surface 501. The gridlines on the image are sometimes a disturbance when the image is observed. An effective way of eliminating the gridlines is to move or oscillate the grid in the gridline traversing direction during an X-ray exposure. According to this method, the gridlines are blurred and only the shadow image of the shooting object appears on the image reception surface. However, this method requires a mechanism for moving the grid during an X-ray exposure, speed control for appropriately moving the grid, a countermeasure for oscillation, a countermeasure for noise generated by the moving mechanism, and so forth, thus requiring a high cost. In addition, since the timing of radiographing has to be adapted to the movement of the grid mechanism, there is a problem of less flexibility.

Meanwhile, since the image of gridlines is multiplied by the shadow image of the shooting object, it can be converted to addition data by logarithmic transformation. Therefore, if the image of shooting object having gridlines is acquired as a digital image, it is possible to remove the gridline data by image processing.

In general, the grid is constructed by arranging lead strips at extremely accurate intervals in one direction. The gridline's shadow image on an image has a spatially oscillating striped pattern having accurate spatial frequency peaks. Image processing methods for removing such gridline data include: a method disclosed in Japanese Patent Application Laid-Open (KOKAI) No. 2001-189866 where a response of a particular spatial frequency area is reduced by using wavelet transformation; or a method disclosed in Japanese Patent Application Laid-Open (KOKAI) No. 2002-330344 where a gridline component representing the characteristic of the gridlines is predicted and generated, then subtracted from the radiographic image.

In recent years, a so-called direct type X-ray sensor, in which incident X-ray particles directly capture free electrons generated in the semiconductor, is on its way to practical application, and the spatial frequency response (hereinafter referred to as the modulation transfer function (MTF)) of an X-ray image reception system (hereinafter referred to as the X-ray sensor) is improving. The spatial frequency response is improving also in the indirect type X-ray sensor, in which an X-ray intensity is once converted to low-energy fluorescence to be captured. According to the sampling theorem, all the components higher than the Nyquist frequency which is a half of the spatial sampling pitch are folded back to a frequency lower than the Nyquist frequency before they are observed. Therefore, it seems nonsense to improve the MTF more than necessary. However, it is better to improve the MTF as much as possible for a frequency lower than the Nyquist frequency. Therefore, the X-ray sensor's MTF is improved under the assumption that there is almost no component higher than the Nyquist frequency in an object of shooting.

FIG. 11A shows a shadow image of the gridlines. As illustrated, the light transmitting portion and blocking portion create periodical shadow images at accurate interval Tg. FIG. 11B is a schematic view of the spatial spectrum of FIG. 11A. Since the shadow image of the gridlines is a periodic function, FIG. 11B shows the 1/Tg line spectrum peak that is a fundamental wave, as well as the n-th (n=2, 3, . . . ) line spectrum peaks (n-th harmonics) of the fundamental wave. As the X-ray sensor's MTF is improved as mentioned above, the n-th line spectrum peaks are also transmitted without being reduced, and appear on the image. The conventional image processing technique of reducing the gridlines gives almost no consideration on removing the gridline component that corresponds to the n-th line spectra. The only thing that considers this matter is Japanese Patent Application Laid-Open (KOKAI) No. 2003-38481, which discloses a method of setting a frequency of gridlines in a way that the fundamental wave and second harmonic component of the gridlines have an almost equal frequency in the sampled image signal.

SUMMARY OF THE INVENTION

The present invention has been proposed in view of the above-described problems, and has as its object to remove a fundamental wave component and harmonic component of the gridlines from a radiographic image, and to acquire a radiographic image having little effect of gridlines even when an X-ray sensor having a high MTF is used.

According to one aspect of the present invention, there is provided an image processing method comprising: a measuring step of measuring a fundamental frequency and at least one harmonic frequency of gridlines in a radiographic image; a generating step of generating a grid image by fitting a gridline model, which takes the fundamental frequency and the harmonic frequency measured in the measuring step into consideration, based on the radiographic image; and a removing step of removing the gridlines from the radiographic image using the grid image generated in the generating step.

According to another aspect of the present invention, there is provided a grid sorting method comprising: a measuring step of measuring a fundamental frequency and at least one harmonic frequency of gridlines in a radiographic image which is obtained by radiographing a grid only; an acquisition step of calculating a power spectrum with respect to each of a first direction traversing the gridlines and a second direction parallel to the gridlines, calculating a sum of the power spectrum besides the power spectrum of the fundamental frequency portion and the harmonic frequency portion of the gridlines with respect to each direction, and acquiring a ratio of the sums of these power spectra; and a determining step of determining good or poor quality of the grid based on the ratio acquired in the acquisition step.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

FIGS. 12A and 12B are explanatory views of frequency variation when gridlines and their second harmonic are sampled;

FIGS. 14A and 14B are explanatory views describing a difference in vertical and horizontal spectra of a grid image;

DETAILED DESCRIPTION OF THE PREFERRED EMBODIMENTS

Figure 1:
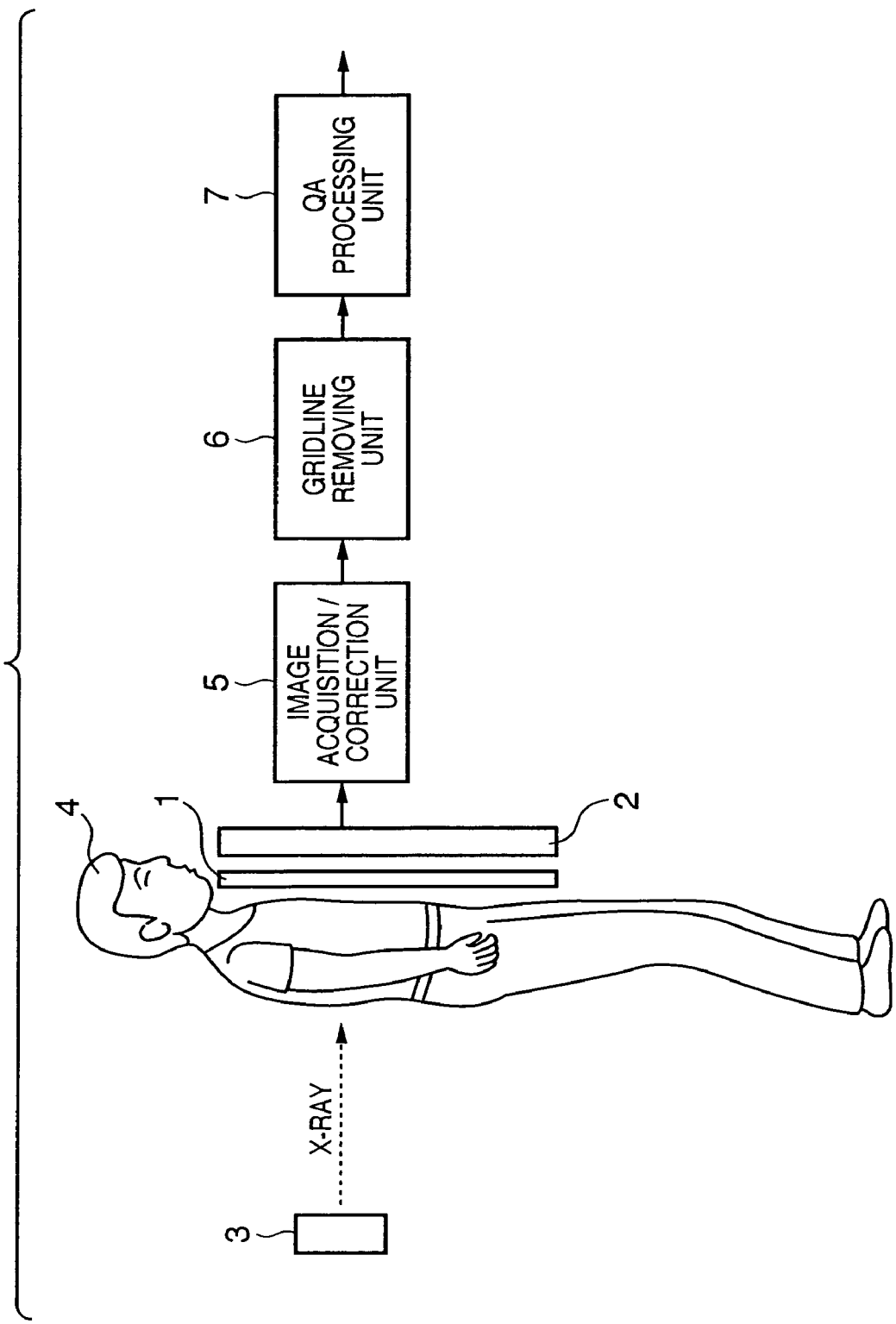
FIG. 1 is a block diagram showing a construction of a radiographic apparatus according to a first embodiment.

Preferred embodiments of the present invention will now be described in detail in accordance with the accompanying drawings.

Summary of Embodiments

Before each embodiment is described in detail, a summary of each embodiment is provided. In order to deal with the aforementioned second or higher harmonic component of the gridlines, the embodiment employs a model that takes a second or higher harmonic component into consideration to generate a gridline model, and predicts gridlines by performing parameter adjustment of the model. Based on the predicted gridlines, the gridline component is removed.

Furthermore, an appropriate parameter of the gridline model is determined using the aforementioned model, based on the fact that a scatter value of an image component from which the gridlines are appropriately removed is roughly equal in the gridline traversing direction and gridline parallel direction. This utilizes the basic concept that the local power of an image signal component of a normal object of shooting has no orientation and is isotropic. Note that the scatter (average of the sum of squares) and power have the same meaning. It is mathematically proven that the summation of power spectra is equal to a scatter value of signal components.

In the basic process of the embodiment, the following processing (1) to (7) are executed. Details of each processing will be apparent from the detailed description of the respective embodiments.

(1) The first line spectrum peak Fh1, which is a gridline fundamental wave component of an image, is correctly measured.

(2) Based on the frequency of the first line spectrum peak and a sampling pitch of the X-ray sensor, the second line spectrum peak frequency Fh2 that is a second harmonic component frequency is calculated.

(3) A filter for extracting the first line spectrum peak frequency and the second line spectrum peak frequency is formed.

(4) Line data in the gridline traversing direction is extracted from image data, and the filter is used to roughly extract a signal including both the first line spectrum peak and the second line spectrum peak.

(5) The roughly extracted signal component is divided into plural small blocks, and the data of each block is fitted into a gridline signal model having a first gridline component and a second gridline component. In this stage, a parameter of the model is adjusted in a way that the fitting error is approximately equivalent to a scatter value of the image data in the gridline parallel direction corresponding to the block of interest.

(6) The signal data obtained by the foregoing fitting is gridline data. The gridline data is subtracted from the original image data, thereby obtaining image data from which gridlines are appropriately removed.

(7) The processing (4) to (6) are repeated for each line of the image.

The generation process of the second harmonic frequency Fh2 is described with reference to FIGS. 12A and 12B. FIG. 12A shows positions of various spectrum peaks. The abscissa expresses a spatial frequency. More specifically, a spatial frequency of sampling carrier Fs (−Fs), a spatial frequency of the grid Fg (−Fg), and a spatial frequency of the second harmonic 2Fg (−2Fg) are shown. The grid signal being modulated (multiplied) by the sampling carrier is considered sampling. Therefore, as shown in FIG. 12B, the frequency of gridlines changes by the convolution of both and becomes a frequency lower than the Nyquist frequency Fn (=Fs/2), which is a half of the sampling frequency, then observed (sampling theorem).

Figure 13:
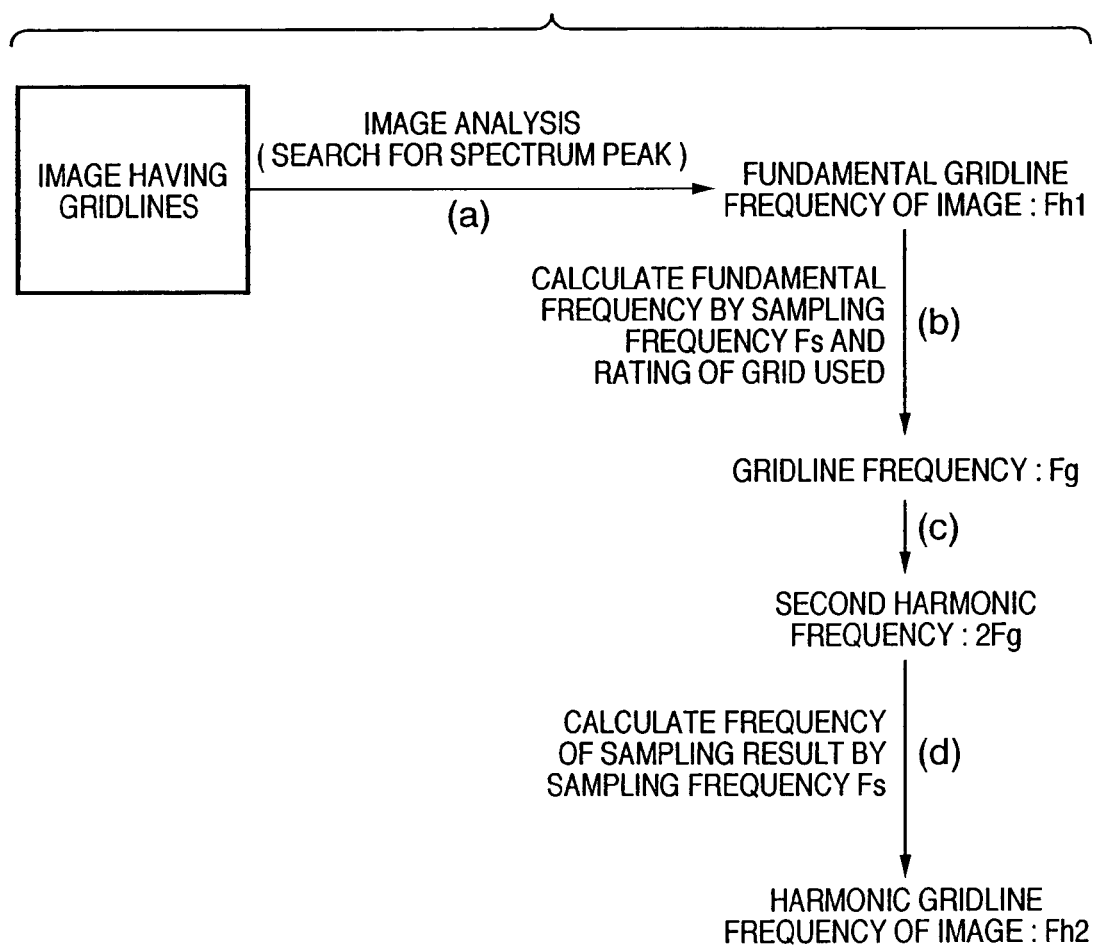
FIG. 13 is an explanatory view describing a frequency calculation procedure when gridlines and their second harmonic are sampled.

Herein, a specific calculation method of Fh1 and Fh2 is described with reference to FIG. 13 which shows the flow of the calculation. Referring to FIG. 13, image data having gridlines is given as input data. The image data is subjected to Fourier transformation to search for a spectrum peak, thereby obtaining the fundamental gridline frequency Fh1 of the image ((a) in FIG. 13). Next, a fundamental frequency Fg of the grid that generates the frequency Fh1 is calculated ((b) in FIG. 13). In this case, it is necessary to know in advance the approximate position of the grid's spatial frequency Fg, but it can easily be obtained. More specifically, acquiring the rating of a normally used grid sufficiently serves the purpose.

Even if the rating of the grid (interval of the lead strips produced) is obtained, there is usually a space between the grid and the X-ray sensor. Since the gridlines are magnified by radiography, the shadow image of the gridlines on the X-ray sensor does not come out accurately as the rating. Further, a production error exists as well. In the process (a) in FIG. 13, a gridline frequency is measured. However, an approximate gridline frequency range can be defined. This example assumes that the positions of the frequencies Fn<Fg<Fs are known in advance. In the aforementioned process (1), Fh1 which is measured by analyzing the image data is the strongest fundamental spatial frequency of the grid. Fh1 is obtained by modulating the grid's fundamental frequency signal Fg by sampling carrier Fs, and is calculated by the following equation:

$$|Fh1|=|K \cdot Fs-Fg|; K=1,2,3 \ldots, \text{select } K \text{ satisfying} \\ |Fh1| \leq Fs/2 \quad (1)$$

In this embodiment, since Fh1 is first measured from the image data, Fg has to be calculated back using the relation Fn<Fg<Fs. Fg is calculated by the following equation:

$$Fg=|K \cdot Fs-Fh1|; K=1,2,3 \ldots, \text{select } K \text{ satisfying} \\ Fn<Fg<Fs \quad (2)$$

In the gridline frequency Fg obtained in the foregoing manner, it is apparent that the second harmonic frequency becomes exactly "2Fg" ((c) in FIG. 13). The spatial frequency peak of 2Fg after sampling is performed is calculated by the following equation ((d) in FIG. 13):

$$|Fh2|=|K \cdot Fs-2Fg|; K=1,2,3 \ldots, \text{select } K \text{ satisfying} \\ |Fh2| \leq Fs/2 \quad (3)$$

In the following first embodiment, a filter is formed using Fh1 and Fh2 calculated in the foregoing manner, and image data obtained by filtering with the formed filter is fitted into a gridline signal model which takes the fundamental spatial frequency Fh1 and second harmonic frequency Fh2 of the gridlines into consideration. The signal data that is gridline data obtained by fitting is subtracted from the original image data, and image data from which gridlines are appropriately removed is obtained.

The fitting process (5) in the above-described basic process is performed under the assumption that the gridline's power (scatter value) is isotropic. In the second embodiment, the characteristic of the grid itself (aerotropy of the power (scatter) in the grid parallel direction and grid traversing direction) is taken into consideration, thereby performing even more accurate gridline removal. More specifically, the above-described basic process utilizes the concept that power of shooting object image data basically has no orientation and is isotropic. However, since the shadow image of the grid is not always isotropic, the aerotropy is focused in performing gridline removal.

As mentioned above, the grid is constructed by arranging lead strips at equal intervals. To properly fix the lead strips, a highly radiolucent intermediate substance, such as aluminum, resin, wood, paper or the like is inserted. Depending on the processing precision of the lead strips, and the material, processing precision and assembling precision of the intermediate substance, a signal component other than the gridlines exists in the obtained shadow image of the grid. In addition, since the grid is constructed with lead strips arranged in one direction, there is a possibility that the image signal component of the shadow image may lose its isotropy.

FIGS. 14A and 14B schematically show power spectra of image signals in a case where a grid is radiographed. Line 510 in FIG. 14A indicates a power spectrum of an image signal in the gridline traversing direction, which includes two line spectra indicative of the grid fundamental frequency and a peak of the second harmonic gridline. Line 511 indicates a power spectrum of an image signal in the gridline parallel direction, which includes no gridlines. FIG. 14A shows that the power spectra in the gridline traversing direction and gridline parallel direction are almost the same except for the existence of gridlines.

Line 512 in FIG. 14B indicates a power spectrum of an image signal in the gridline traversing direction in a case where another grid is radiographed. Due to the effects of manufacturing precision of the grid and the material of the intermediate substance, the spectrum includes a spectrum peak 514 which is not supposed to exist in the original gridlines. Line 513 indicates a power spectrum of an image signal in the gridline parallel direction. In FIG. 14B, there is a large difference between the power spectrum in the gridline parallel direction and the power spectrum in the gridline traversing direction.

In the second embodiment, a grid quality (GQ) value is obtained in advance as a factor representing the isotropy of the noise characteristic of the grid's shadow image. This value is used as a parameter for removing gridlines.

Figure 15:
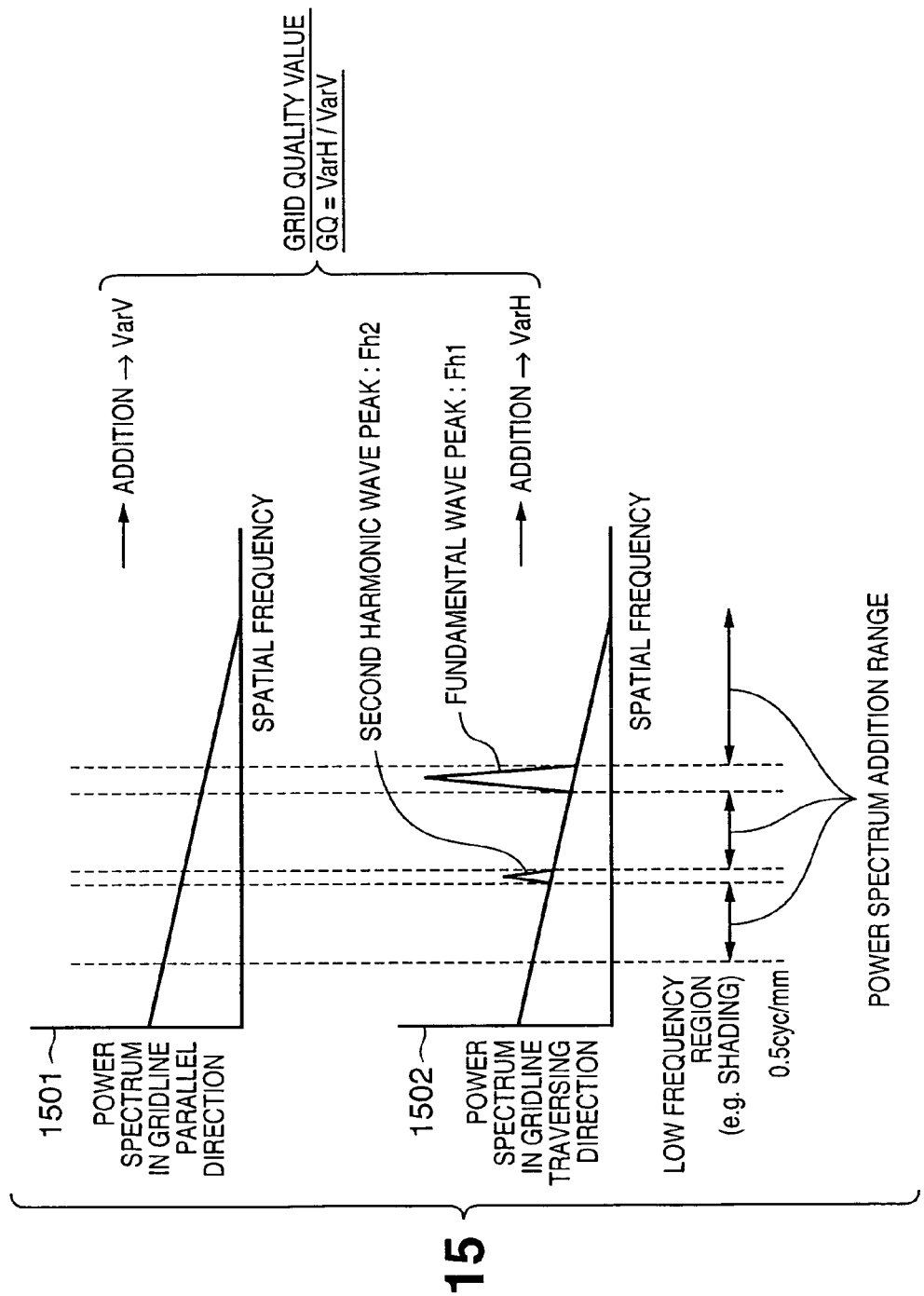
FIG. 15 is an explanatory view of the GQ value calculation.

FIG. 15 shows a method of calculating the GQ value. Referring to FIG. 15, a graph 1501 shows a power spectrum in the gridline parallel direction, and a graph 1502 shows a power spectrum in the gridline traversing direction. The power spectrum in the grid-traversing direction includes the aforementioned grid fundamental frequency peak Fh1 and second harmonic peak Fh2. The GQ value is defined by a ratio of a scatter value in the gridline traversing direction to a scatter value in the gridline parallel direction. In this case, in order to eliminate a difference due to a component caused by the gridlines and a difference in the shape of the X-ray radiation distribution at the time of radiography, components in the low spatial frequency region (0.5 cyc/mm or lower) and components around Fh1 and Fh2 are disregarded, and the power spectrum other than these regions is added to obtain the scatter value of each direction. In FIG. 15, VarV and VarH are obtained as an addition value, and the GQ value is obtained by the following equation:

$$GQ = \mathrm{Var}H / \mathrm{Var}V \quad (4)$$

Therefore, in the following second embodiment, the process (5) of the above-described basic processes (1) to (7) is changed as follows:

(5) The roughly extracted signal component is divided into plural small blocks, and the data of each block is fitted into a gridline signal model having a first gridline component and a second gridline component. In this stage, the parameter of the model is adjusted in a way that the fitting error becomes GQ-multiplies of the scatter value of the image data in the gridline parallel direction corresponding to the block of interest.

For a grid model fitting method, a method of adjusting the number of data points (first and second embodiments) and a method of selecting an appropriate one from plural models (third embodiment) are available. Furthermore, in the fourth embodiment, the GQ value is actively utilized to define the quality of a grid, and grids are sorted in advance so as not to use a poor-quality grid (having a GQ value not close to 1).

Hereinafter, each embodiment is described in detail. Note, although the following embodiments describe a case where only the second harmonic is taken into consideration, it is apparent to those who are skilled in the art that the third, fourth, . . . , n-th harmonic can also be taken into consideration.

First Embodiment

FIG. 1 is a block diagram showing a construction of a radiographic apparatus according to the first embodiment. In FIG. 1, numeral 1 denotes an anti-scatter grid (hereinafter referred to as a grid); and 2, an X-ray image sensor where a plurality of pixels are arranged in a matrix. Assume that the pixel interval of the matrix of the X-ray image sensor 2 is T, and the sampling spatial frequency is Fs=1/T. Numeral 3 denotes an X-ray generator; and 4, an object of shooting which is a human body in this case. The X-ray generator 3 is controlled by an X-ray generation controller including a high-voltage generator (not shown), and radiates an X-ray to the object of shooting 4, grid 1, and X-ray image sensor 2 in accordance with an operation of an operator. The X-ray image sensor 2 is driven in synchronization with the X-ray generation. While an X-ray is irradiated, the X-ray image sensor 2 accumulates in each pixel the charge corresponding to the amount of X-ray transmitted through the object of shooting.

The accumulated charge value of each pixel is converted to a digital value and outputted as image data.

Numeral 5 denotes an image acquisition/correction unit, which acquires image data outputted by the X-ray image sensor 2 and performs various corrections. Various corrections herein mean correction of a dark output value of the image data outputted by the X-ray image sensor, correction of gain variation of each pixel, and correction of defective pixels. The correction of a dark output value is realized by acquiring image data that has not been X-ray-irradiated in advance or immediately after an X-ray image acquisition, and subtracting the data from the X-ray image which is obtained by radiographing the object of shooting. The correction of gain variation is realized by dividing an X-ray image obtained by radiographing the object of shooting by the image data obtained in a case where X-ray irradiation is performed with no object of shooting. The correction of defective pixels is realized by grasping the position of a defective pixel in a manufacturing stage, then predicting the pixel value based on peripheral pixel values, and correcting the defective pixel value.

The image data corrected by the image acquisition/correction unit 5 is supplied to a gridline removing unit 6 to be subjected to gridline removal. Next, a QA processing unit 7 performs quality assurance (QA) processing for easy diagnosis. Then, the data is outputted to an external storage device or an external image printer or the like. The QA processing herein means generally performed image processing, such as gradation conversion processing, frequency emphasizing processing, image extraction processing, reduction, enlargement and the like.

The above-described image acquisition/correction unit 5, gridline removing unit 6, and QA processing unit 7 are realized by a computer apparatus which executes processing in accordance with a program stored in, e.g., a memory. Hereinafter, the gridline removing unit 6, which is the characteristic configuration of the first embodiment, is described in detail.

Figure 2:
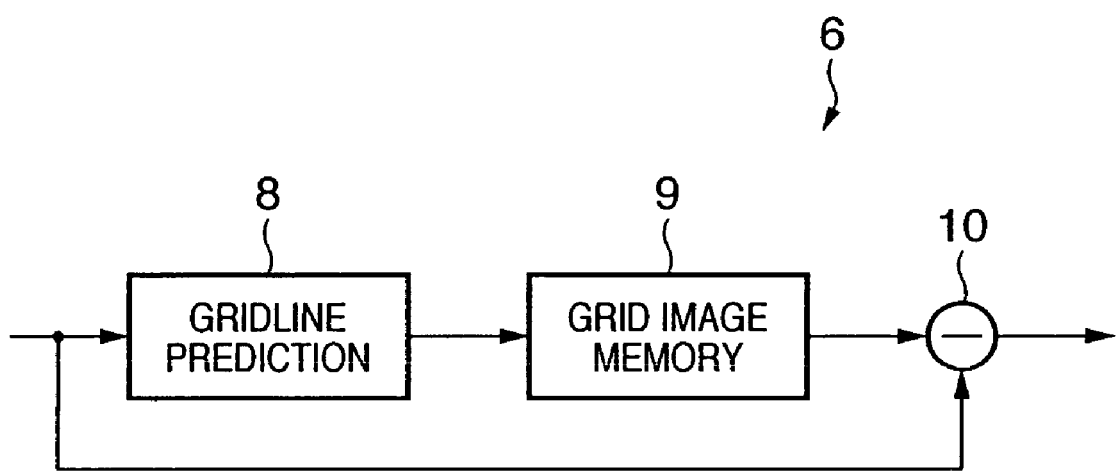
FIG. 2 is a block diagram showing a detailed construction of a gridline removing unit.

FIG. 2 explains the internal construction of the gridline removing unit 6 by further dividing the construction into smaller blocks. In the gridline removing unit 6, a gridline predicting unit 8 predicts gridlines based on inputted image data, and stores the gridline data in a grid image memory 9. In a subtracter 10, the content stored in the grid image memory 9 is subtracted from the inputted image data, and an image from which gridlines are removed is outputted.

Next, the processing in FIG. 2 is described in detail with reference to the flowchart in FIG. 3. In step S101, an existence and direction of a grid is determined based on the inputted image data. Although the existence and direction of a grid can be determined by a mechanical structure, this example performs image data analysis to determine the existence and direction of the grid. More specifically, a horizontal line and a vertical line are arbitrarily selected from the image, and frequency characteristics of the selected lines are obtained by fast Fourier transformation (FFT). Based on the obtained frequency characteristics, it is determined that the direction of the line having a strong peak includes gridlines. If neither the horizontal nor vertical line has a strong peak, it is determined that there is no gridlines, and the control ends (not shown).

Figure 4:
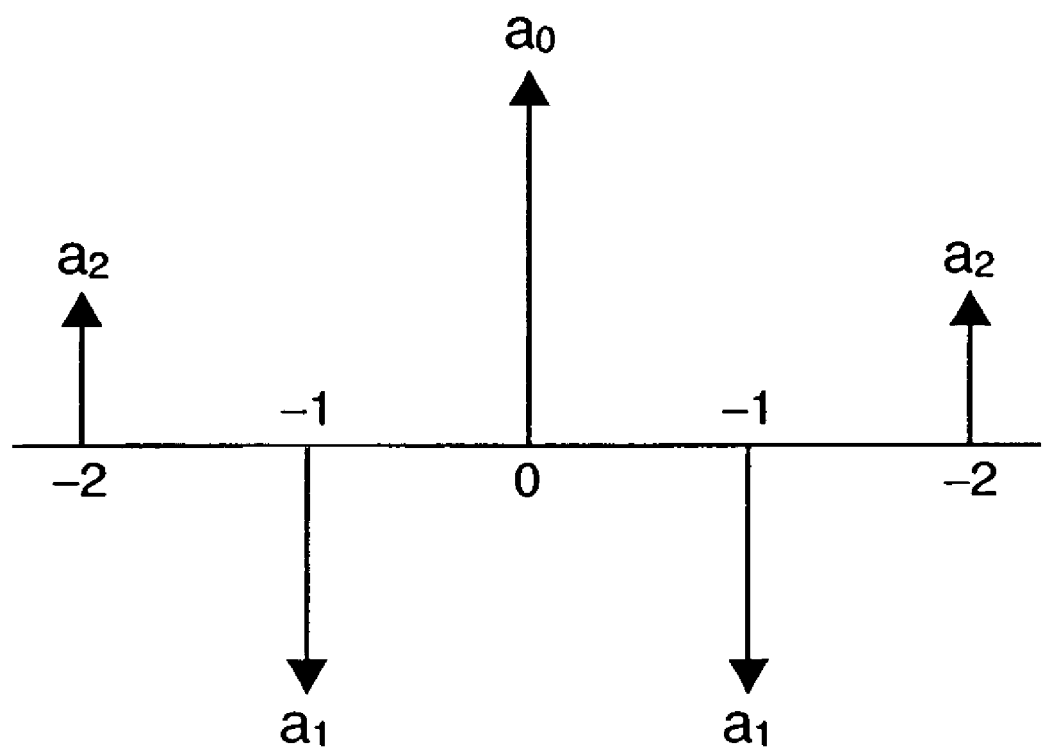
FIG. 4 is an explanatory view of coefficients of a FIR filter adopted by the first embodiment.

Based on the result obtained in step S101, in step S102 Fourier transformation is further performed in detail (with increased number of points) with respect to the direction of line including the gridlines, and the gridline frequency Fh1 on the image is measured. In step S103, the frequency Fh2 which is the second harmonic component is calculated. The second harmonic component Fh2 is calculated by, as mentioned above, obtaining the gridline frequency Fg using equation (2), doubling Fg and calculating equation (3). Next in step S104, a finite impulse response (FIR) filter is formed for roughly extracting a gridline signal. A FIR filter having a symmetrical coefficient is selected so as not to change the phase of the signal component. FIG. 4 shows an arrangement of coefficients $a_0$ to $a_2$ of the five-point FIR filter adopted by the first embodiment. The frequency characteristic G(f) of the filter is expressed by the following equation (5), where the sampling pitch of the X-ray sensor is T:

$$G(f)=a_0+2a_1\cos(2\pi fT)+2a_2\cos(2\pi f2T)=a_0+2a_1\cos(2\pi fT)+2a_2(2\cos^2(2\pi fT)-1) \quad (5)$$

The parameters $a_0$ to $a_2$ in equation (5) are determined as follows:

G(0)=0; eliminate a direct current component of the image and a low-frequency component of the image G(Fh1)=1; accurately extract a gridline component of the image G(Fh2)=2; accurately extract gridline second harmonic component of the image By inserting these three conditions to equation (5) and solving the simultaneous equations, the following equation (6) is obtained:

$$a_2 = \frac{1}{4(\cos(2\pi Fh1\cdot T)+\cos(2\pi Fh2\cdot T)-\cos(2\pi Fh2\cdot T)\cos(2\pi Fh1\cdot T)-1)} \quad (6)$$

$$a_1 = -2a_2(\cos(2\pi Fh1\cdot T)+\cos(2\pi Fh2\cdot T))$$

$$a_0 = -2(a_1+a_2)$$

By equation (6), the coefficient of the FIR filter shown in equation (5) is obtained, and the FIR filter is formed.

Upon forming the FIR filter as described above, gridline removal is performed in steps S105 to S113. In step S105, it is determined whether or not all the image data has been processed. If there is an unprocessed line, the control proceeds to step S106 for extracting line data of the line of interest in the gridline traversing direction. In the first embodiment, the line data is generated by average values of m lines of pixel arrays arranged in the gridline parallel direction. At the same time, a scatter value for each of the m lines of pixel arrays is calculated. In other words, an average value of pixels arranged in the vertical m lines and a scatter value of the pixels in the gridline parallel direction that are used in averaging are obtained for the number of pixels in the line, and line data is formed by the array of average pixel values.

Figure 16:
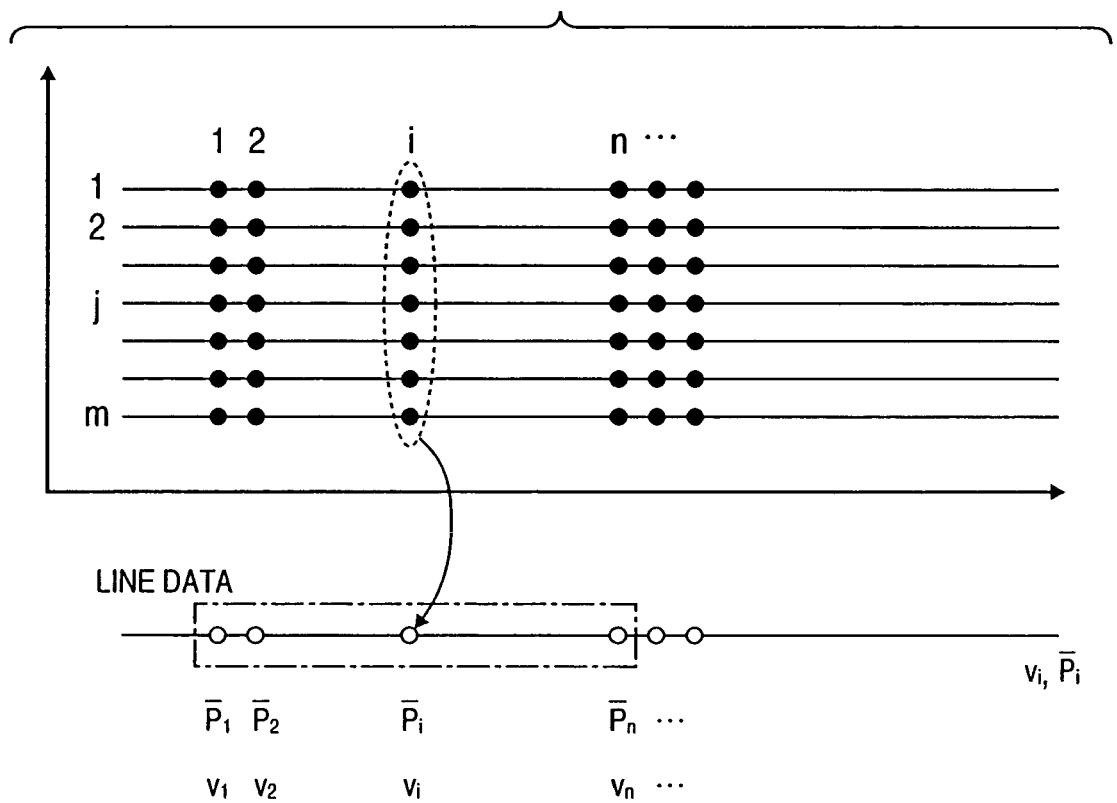
FIG. 16 is an explanatory view on calculation of a pixel average value and a scatter value at the time of fitting processing.

FIG. 16 explains the above-described state. Pixel values are averaged (equation (A)) with respect to each pixel array consisting of m number of pixels, arranged in the gridline parallel direction (Y direction), of the m number of lines (including the line of interest in the middle) arranged in the gridline traversing direction (X direction). Based on the obtained pixel values of the line of interest, line data is generated. With respect to this pixel array, a scatter value is obtained by equation (B).

In step S107, the line data obtained in step S106 is subjected to filtering of the FIR filter obtained by equation (6), thereby roughly extracting gridline data. In step S108, in the gridline data that has been roughly extracted, a portion (hereinafter referred to as a faulty portion) that cannot be supplied to the subsequent fitting calculation due to the effect of an image edge or the like is determined. More specifically, a proper threshold value is used to determine whether or not the roughly extracted signal amplitude is abnormally high and the phase variation is abnormally large, and if so, the data of this position is not used in the subsequent calculation. To determine the amplitude and the amount of phase variation, for instance, a filter (differential filter) where the phase shifts by 90 degrees is used, and variation of the amplitude value and phase value is determined based on the original signal A and the differential filter's output signal B. To be more specific, variation of the amplitude value is obtained by calculating a root of the sum of squares of the original signal A and the differential filter's output signal B. By looking at the variation of $\text{Tan}^{-1}(B/A)$, the phase value is obtained, and by checking the variation of the value, the phase variation can be obtained (to be more accurate, since the output of calculation $\text{Tan}^{-1}$ generally ranges from $-\pi$ to $+\pi$ due to its calculation characteristic, it is necessary to convert the value to a normal value (the range is not narrowed) that takes the vector rotation into consideration, i.e., convert to a continuous value (called phase unwrapping)).

In step S109, the gridline data besides the faulty portion is divided into smaller blocks (normally about 10 to 30 pixels). This embodiment assumes that one block has n numbers of pixels as shown in B of FIG. 16. Although the gridline itself is stable as a whole, due to an effect of a scattered radiation component of the object of shooting, there is a case that the signal is unsteady in a large scale even if the signal seems steady in a partial scale. To prevent the unsteady signal from fitting, the data is divided into small blocks that can be regarded steady. Note, although this embodiment removes the faulty portion before the gridline data is divided into small blocks (so as to avoid loss), the data may be first divided into small blocks then a faulty block may be removed. In step S110, fitting is performed to extract grid data with respect to each of the obtained blocks.

The grid's equation model G1(x) employed in the first embodiment is expressed by the following equation. In this model, the measured fundamental frequency and the harmonic frequency of the gridlines are taken into consideration.

$$G_1(x)=c_1\cos(2\pi Fh1\cdot x)+d_1\sin(2\pi Fh1\cdot x)+c_2\cos(2\pi Fh2\cdot x)+d_2\sin(2\pi Fh2\cdot x) \quad (7)$$

When an input data sequence $\{x_i, y_i; i=1, 2, \ldots, n\}$ of the point n is given, respective parameters $c_1, c_2, d_1$ and $d_2$ of the model can be obtained by calculating the following simultaneous equation (8):

$$\begin{bmatrix} \Sigma\cos^2(\omega_1 x_i) & \Sigma\cos(\omega_1 x_i)\sin(\omega_1 x_i) & \Sigma\cos(\omega_1 x_i)\cos(\omega_2 x_i) & \Sigma\cos(\omega_1 x_i)\sin(\omega_2 x_i) \\ \Sigma\cos(\omega_1 x_i)\sin(\omega_1 x_i) & \Sigma\sin^2(\omega_1 x_i) & \Sigma\sin(\omega_1 x_i)\cos(\omega_2 x_i) & \Sigma\sin(\omega_1 x_i)\sin(\omega_2 x_i) \\ \Sigma\cos(\omega_1 x_i)\cos(\omega_2 x_i) & \Sigma\sin(\omega_1 x_i)\cos(\omega_2 x_i) & \Sigma\cos^2(\omega_2 x_i) & \Sigma\cos(\omega_2 x_i)\sin(\omega_2 x_i) \\ \Sigma\cos(\omega_1 x_i)\sin(\omega_2 x_i) & \Sigma\sin(\omega_1 x_i)\sin(\omega_2 x_i) & \Sigma\cos(\omega_2 x_i)\sin(\omega_2 x_i) & \Sigma\sin^2(\omega_2 x_i) \end{bmatrix} \begin{bmatrix} a_1 \\ b_1 \\ a_2 \\ b_2 \end{bmatrix} = \begin{bmatrix} \Sigma(y_i\cos(\omega_1 x_i)) \\ \Sigma(y_i\sin(\omega_1 x_i)) \\ \Sigma(y_i\cos(\omega_2 x_i)) \\ \Sigma(y_i\sin(\omega_2 x_i)) \end{bmatrix} \quad (8)$$

Herein, $\omega_1=2\pi Fh1$, $\omega_2=2\pi Fh2$, and $\Sigma$ indicates addition of n numbers.

In step S110, fitting calculation of each block is performed using equation (8). The fitting calculation of each block is described in detail with reference to the flowchart in FIG. 5 and FIG. 16.

In step S201, an average value of scatters (hereinafter referred to as an average scatter value Vh) of the pixel arrays arranged in the gridline parallel direction in the block of interest is calculated. More specifically, referring to FIG. 16, an average of $V_1$ to $v_n$ is calculated (equation (C)) to obtain an average scatter value Vh. The fitting calculation in this embodiment basically uses the average scatter value Vh. The fitting calculation is performed in a way that the fitting error becomes close to this value. In step S202, fitting calculation is performed by equation (8) using the data in the block. In step S203, a fitting error Vs (average of square error) between the function obtained by fitting in step S202 and original data is obtained (equation (D) in FIG. 16). As is apparent from equation (D), the fitting error Vs is equal to the scatter of the line of interest data from which the gridlines are removed. Therefore, by adjusting the fitting so as to make the fitting error Vs close to the average scatter value Vh, gridlines are removed in a way that the scatter in the gridline traversing direction becomes equal to the scatter in the gridline parallel direction.

In step S204, it is determined whether or not the fitting error Vs exceeds the average scatter value Vh calculated in step S201. If the fitting error Vs has not exceeded the average scatter value Vh, the control proceeds to step S205 where the fitting state is changed. In this embodiment, a pixel value having a largest error between the original data (line data in the block of interest) and the fitted function is excluded from the fitting calculation. This is because, the pixel value excluded from the gridline model in equation (7) is considered to be largely influenced by the object of shooting and noise besides the gridline component. In other words, a pixel assumed to largely include a component other than the gridline component is excluded from the fitting of the gridlines before performing fitting calculation for the purpose of obtaining purer gridline data.

By the foregoing pixel value exclusion, the fitting error Vs in the block increases. In step S206, fitting calculation is newly performed. In step S207, the fitting error Vs is calculated again. Then, the control returns to step S204 to compare the average scatter value Vh with the fitting error Vs again. The foregoing processing is repeated until Vs exceeds Vh in step S204. Then, the control proceeds to step S208, and a fitting parameter having the fitting error Vs closest to the average scatter value Vh is selected from the calculated parameters as the gridline prediction data of the block of interest.

Figure 3:
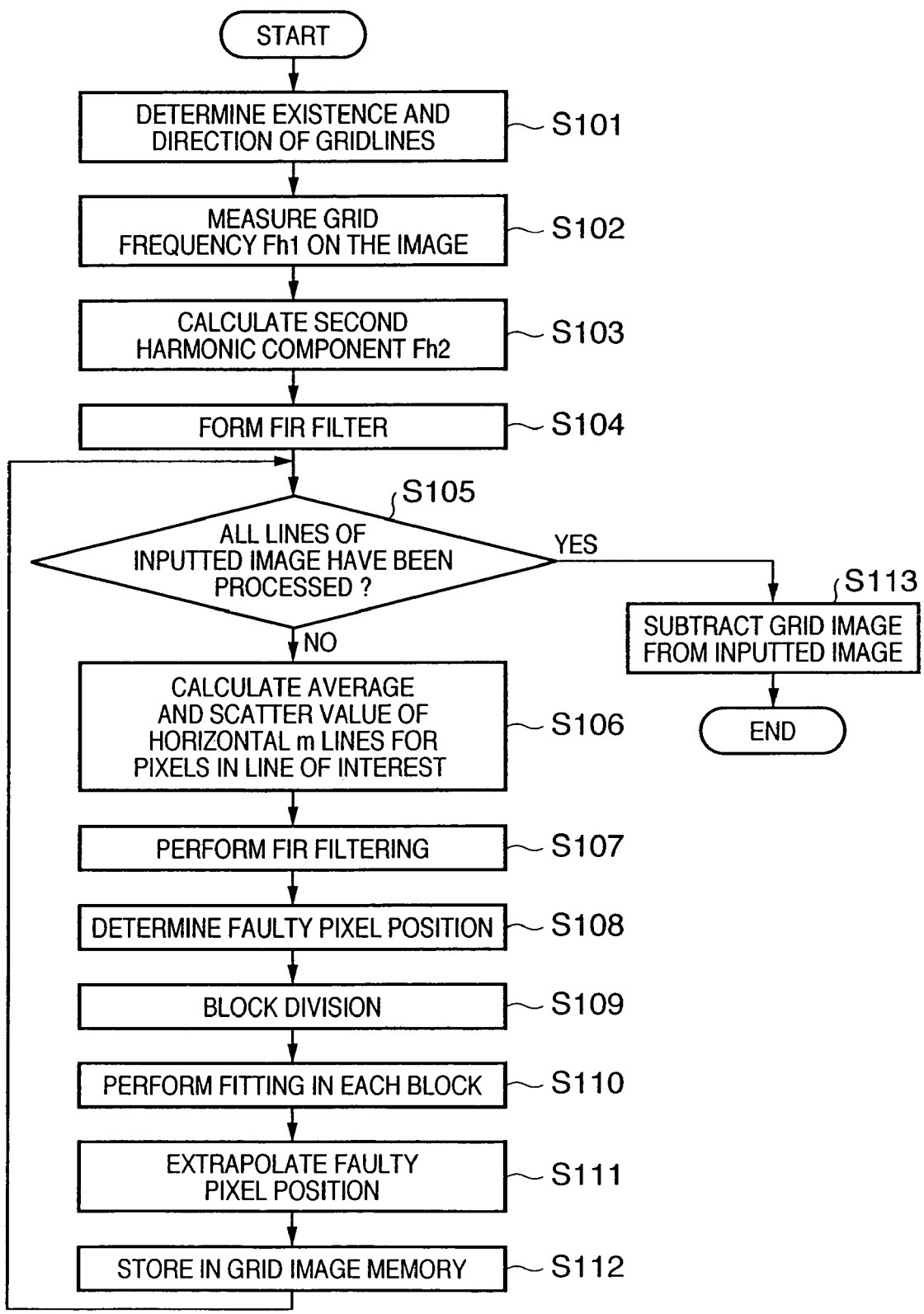
FIG. 3 is a flowchart describing an operation of the gridline removing unit according to the first embodiment.
Figure 5:
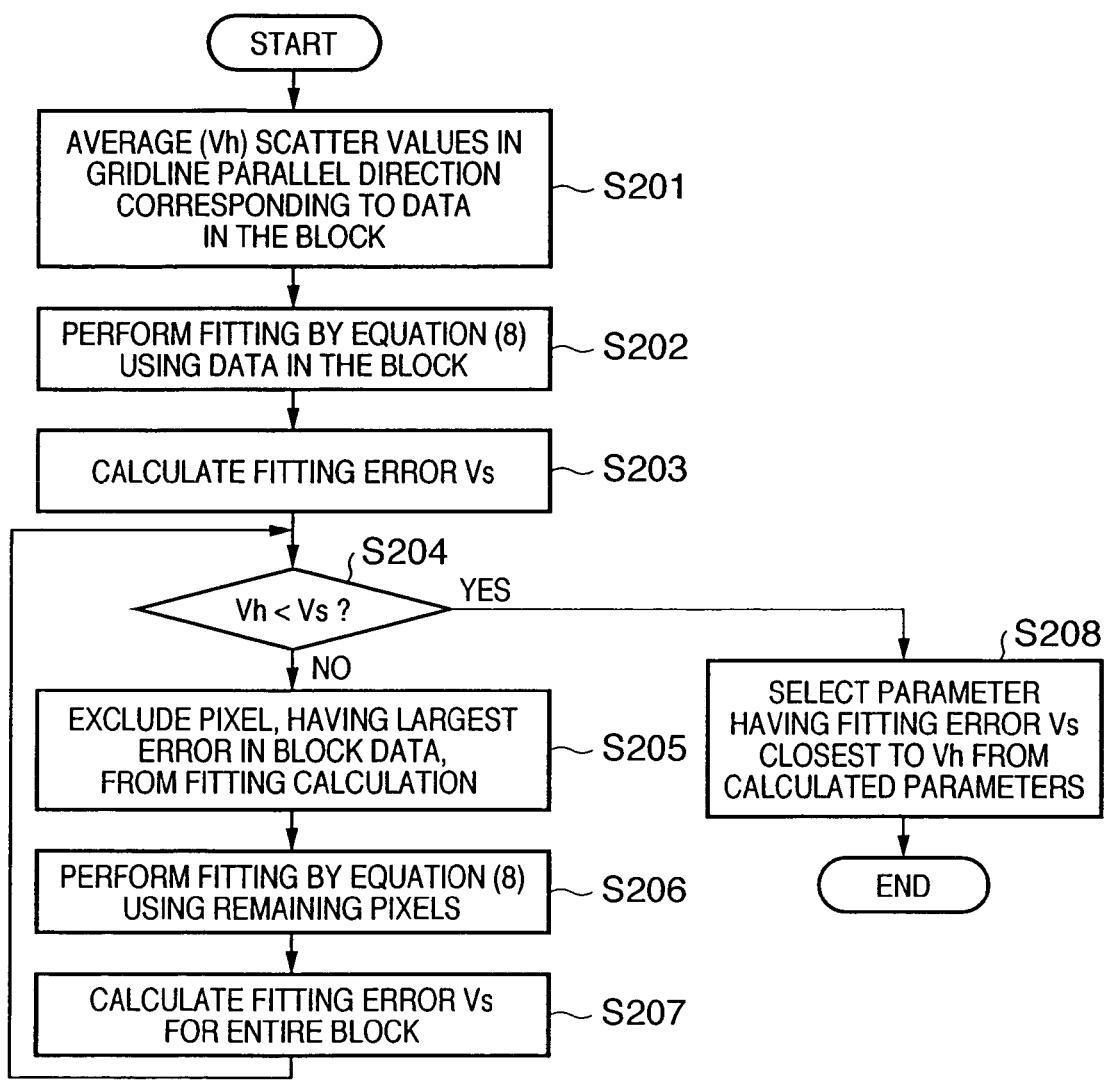
FIG. 5 is a flowchart describing a gridline prediction procedure according to the first embodiment.

In the foregoing manner, the calculation described in FIG. 5 is performed in step S110 of FIG. 3 with respect to each block to generate gridline prediction data of each block. In step S111, the gridline prediction data of the faulty pixel portion, which is excluded in step S108 and is not supplied to fitting, is extrapolated by the fitting parameter of the neighboring block supplied to fitting. In this manner, gridline prediction data of the entire line is completed. In step S112, the completed gridline prediction data is stored in the corresponding line of the grid image memory 9 in FIG. 2. Upon obtaining gridline prediction data of all lines of the inputted image, the control proceeds from step S105 to step S113. The grid image is subtracted from the inputted image by the subtracter 10, and the gridline removal processing ends.

Note, although equations (5) to (8) focus attention to the second harmonic only, it is apparent to those who are skilled in the art that a similar calculation is also possible for the third, fourth, and higher-degree harmonic, and if necessary, similar measures can be performed.

Second Embodiment

In the second embodiment, gridline removal corresponding to the grid quality is performed using the aforementioned GQ value. First, a description is provided on the construction and processing for calculating the GQ value.

Figure 6:
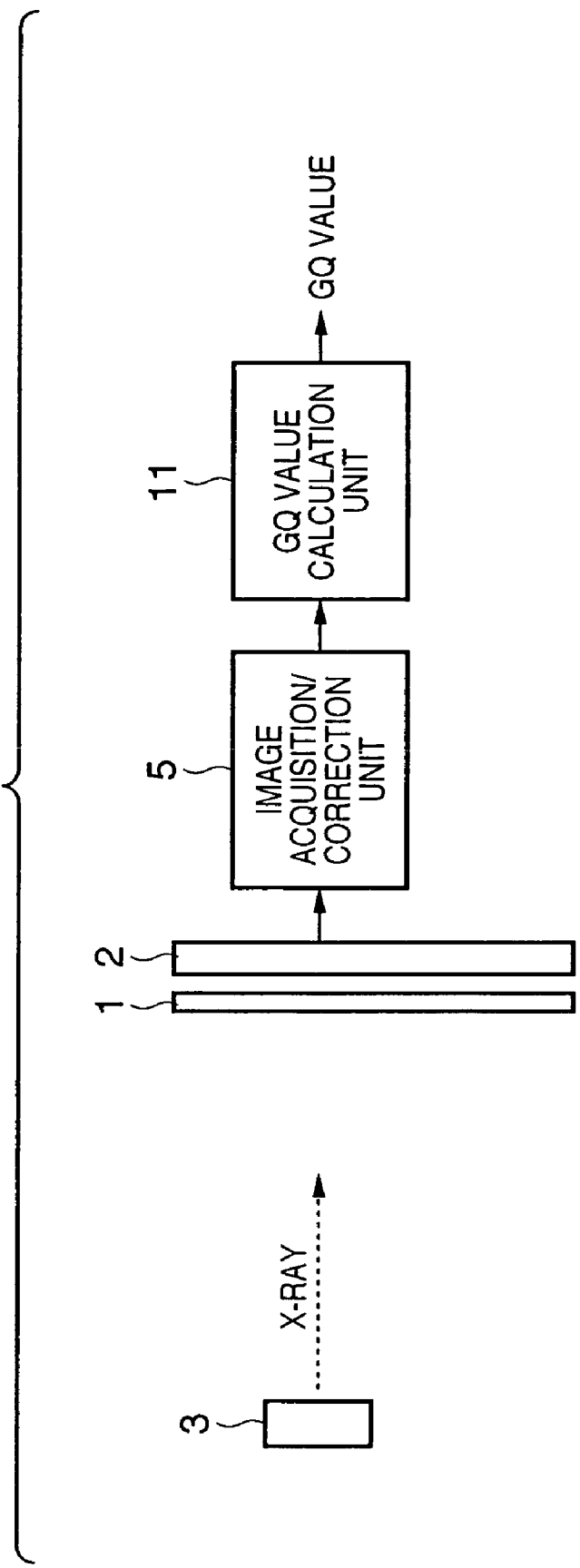
FIG. 6 is a block diagram showing a construction for GQ value calculation according to a second embodiment.

FIG. 6 is a block diagram showing a construction for calculating the GQ value. In comparison with FIG. 1, the object of shooting 4 does not exist and a GQ value calculation unit 11 is added. In this apparatus, the grid is radiographed in advance without an object of shooting, and the shadow image of the grid is analyzed by the GQ value calculation unit 11, thereby obtaining a GQ value. Thereafter, gridline removal is performed using the construction shown in FIG. 1. The second embodiment differs from the first embodiment in that the gridline removing unit 6 uses the GQ value.

In FIG. 6, for the components having the same configuration as those of FIG. 1, the same reference numerals are assigned. Without an object of shooting, the shadow image of the grid 1 is sensed while proper distances and positions are maintained among the X-ray generator 3, grid 1, and X-ray image sensor 2. Then, a GQ Value of the grid 1 is calculated by the GQ value calculation unit 11. Hereinafter, an operation of the GQ value calculation unit 11 is described in detail with reference to the flowchart in FIG. 7. Note that the principle description of the GQ value has already been provided in the <Summary of Embodiments>.

Figure 7:
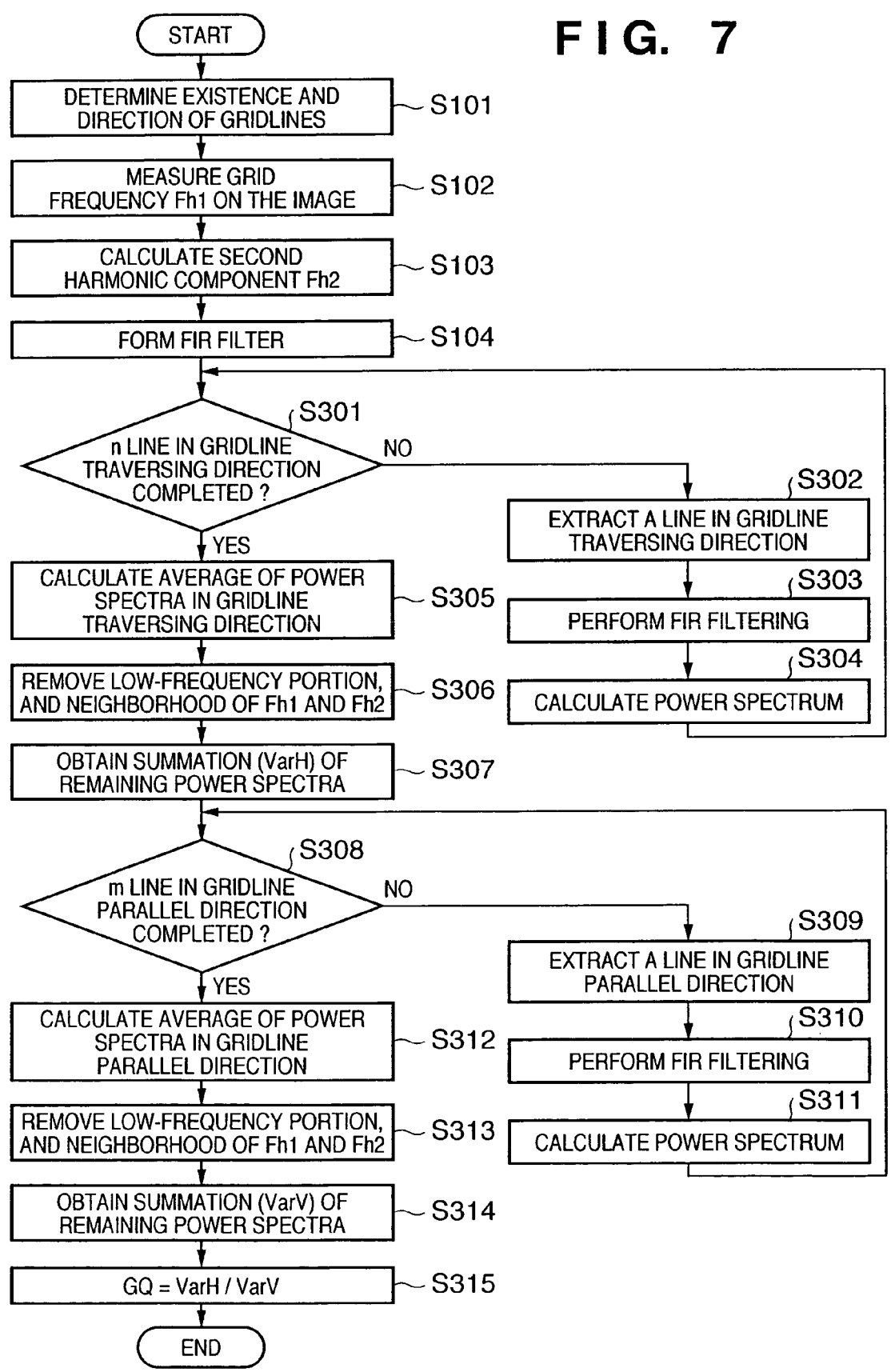
FIG. 7 is a flowchart describing a GQ value calculation procedure.

Steps S101 to S104 in FIG. 7 are the same processing as that described in the first embodiment (FIG. 3). In steps S302 to S307, power spectra in the gridline traversing direction are calculated. More specifically, filtering is performed on the predetermined n lines of data by the FIR filter formed in step S104 (step S302, S303). A power spectrum of the filtered data is calculated (step S304), and an average of the calculated power spectra is obtained (step S301, S305). Then, as described above with reference to FIG. 15, the low-frequency portion and the neighborhood of Fh1 and Fh2 are removed (step S306), and the summation (VarH) of the remaining power spectra is obtained (step S307). In order to appropriately remove the low-frequency portion and the neighborhood of Fh1 and Fh2, it is preferable that the number of points of the Fourier transformation used in calculating the power spectra be 1024 points or more.

Next, in steps S308 to S314, power spectra in the gridline parallel direction are calculated. First, FIR filtering is performed on the predetermined m lines of data in the gridline parallel direction (step S309, S310). A power spectrum of the filtered data is calculated (step S311), and an average of the calculated power spectra is obtained (step S308, S312). Then, as described above with reference to FIG. 15, the low-frequency portion and the neighborhood of Fh1 and Fh2 are removed (step S313), and the summation (VarV) of the remaining power spectra is obtained (step S314). As mentioned above, in order to appropriately remove the low-frequency portion and the neighborhood of Fh1 and Fh2, it is preferable that the number of points of the Fourier transformation used in calculating the power spectra be 1024 points or more. Then, VarH/VarV is calculated in step S315 to obtain a GQ value.

The reason that the FIR filter is used in the above calculation is to efficiently remove the low-frequency component. Therefore, the FIR filter is not an absolute necessity. Furthermore, although the above processing performs power spectrum calculation in units of lines before average processing is performed, the same result can be obtained by performing average processing before the power spectrum is calculated. The GQ value obtained in the foregoing manner represents the quality of an image from which the gridlines are removed, and serves as a fitting target. Note that the "quality of an image" and the "ratio of the power of the image signal component" are closely related to each other. In a case where a normal human body is radiographed as an object of shooting, the aspect ratio of the scatter (power) of the image signal should almost be 1 if it is seen locally. However, if it is largely different, it is assumed that an image having some kind of strong orientation is overlapping on the object of shooting. In this embodiment, what is overlapping is the grid. If an error remains even after the fundamental gridline component is removed, it is considered that some kind of unnecessary component exists in the grid. Since the characteristic of this unnecessary component is unknown, the unnecessary component remains without being removed, resulting in poor quality of an image.

Next, gridline removal processing according to the second embodiment is described. The overall flow of the gridline removal processing according to the second embodiment is the same as that of the first embodiment (FIG. 3). However, fitting processing in step S110 differs from the first embodiment. Hereinafter, fitting processing is described with reference to FIG. 8.

Figure 8:
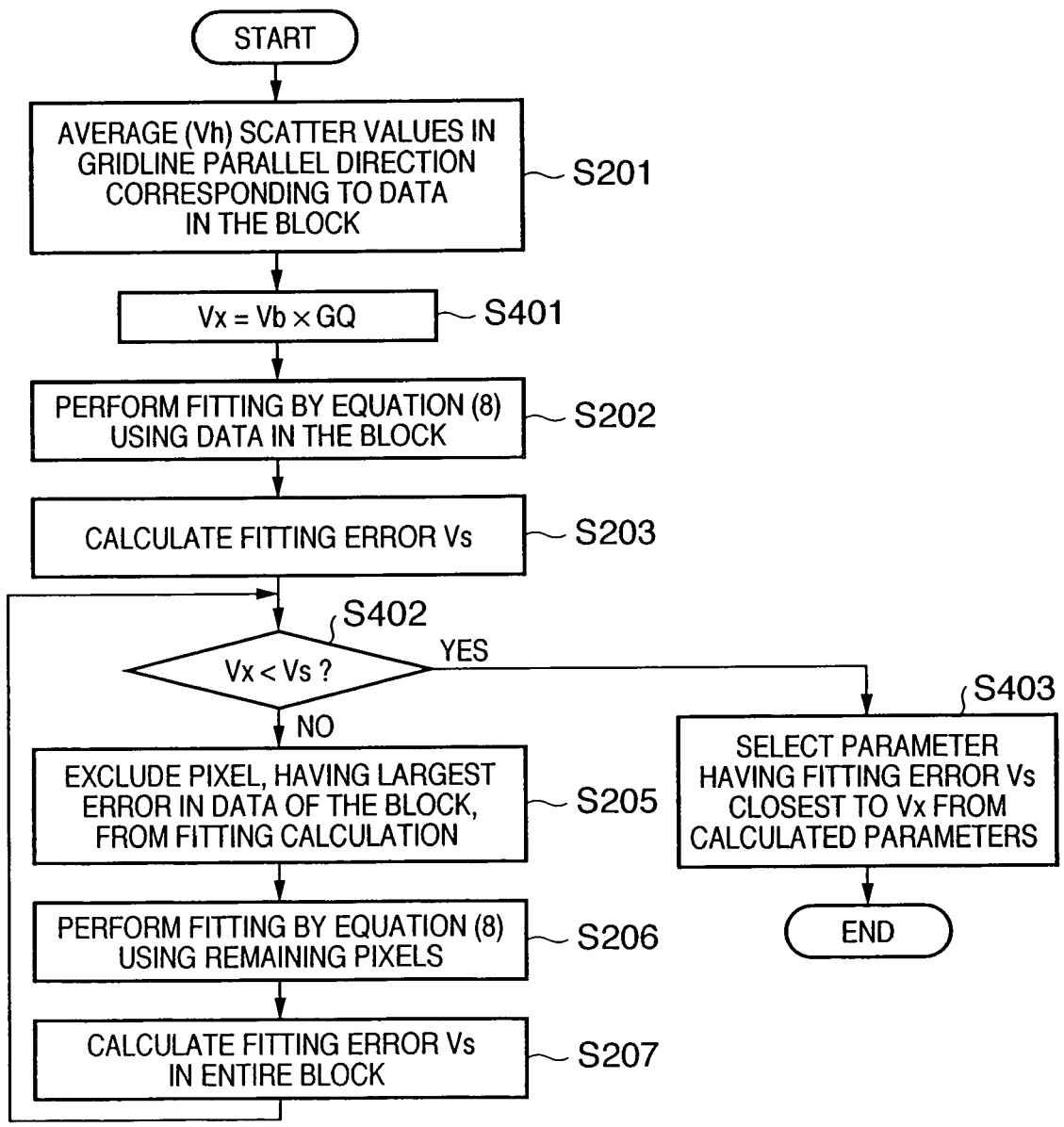
FIG. 8 is a flowchart describing a gridline prediction procedure according to the second embodiment.

Similar to FIG. 5, FIG. 8 shows the gridline fitting method using the GQ value. For the processing same as that of FIG. 5, the same step numerals are assigned. In step S201, the average scatter value Vh in the gridline parallel direction in the block is calculated. The scatter value should be as large as GQ times depending on the quality of the grid. Therefore, in the second embodiment, instead of using the average scatter value Vh as a fitting error target in the gridline traversing direction, a value Vx obtained by multiplying Vh by the GQ value (=Vh×GQ) is used (step S401, S402). Then, the above-described steps S205 to S207 are repeated. When the fitting error Vs exceeds Vx, the control proceeds from step S402 to S403. Then, a fitting error Vs closest to Vx is selected, thereby predicting gridlines.

As described above, according to the second embodiment, gridline prediction is performed taking the characteristic of the grid into consideration. Therefore, gridlines can be removed with higher precision.

Note in the second embodiment, although the GQ value is determined for the entire image and a target value Vx is set, an image may be divided into plural portions, then the GQ value may be obtained for each of the portions to generate a distribution of the GQ values in the image, and gridlines may be predicted by switching the GQ value in accordance with the portion the block belongs to.

Third Embodiment

In the above-described first and second embodiments, the number of data points used is changed for performing appropriate fitting (step S205). However, the method of changing the fitting state is not limited to this. For instance, the model itself can be changed. For instance, besides the model shown in equation (7), the following models (equations (9) to (11)) may be considered.

$$G_2(x) = a_3 \sin(\omega_1 x) + b_3 \cos(\omega_1 x) \quad (9)$$

$$G_3(x) = a_4 x \cos(\omega_1 x) + b_4 x \sin(\omega_1 x) + a_5 \cos(\omega_1 x) + b_5 \sin(\omega_1 x) \quad (10)$$

$$G_4(x) = a_6 x \cos(\omega_2 x) + b_6 x \sin(\omega_2 x) + a_7 \cos(\omega_2 x) + b_7 \sin(\omega_2 x) + a_8 \cos(\omega_1 x) + b_9 \sin(\omega_1 x) \quad (11)$$

Herein, $\omega_1 = 2\pi Fh1$ and $\omega_2 = 2\pi Fh2$.

Equation (9) is a model which does not take the second harmonic into consideration. Equation (10) is a model which takes a linear amplitude variation component into consideration, allowing for some unsteadiness in the block. Equation (11) is a model which takes a linear amplitude variation component into consideration also with regard to the second harmonic component. In each of these models, it is possible to perform fitting by the data sequence given by the simultaneous equation shown in equation (8). Note it goes without saying that, besides these models, various types of model configurations are possible. According to the third embodiment, fitting is performed with respect to n numbers of models, and a model having a remaining error Vs closest to the target value is selected as the most appropriate model for fitting. For the target value, the average scatter value Vh in the gridline parallel direction (first embodiment) or the average scatter value Vh multiplied by GQ (second embodiment) may be employed.

Figure 9:
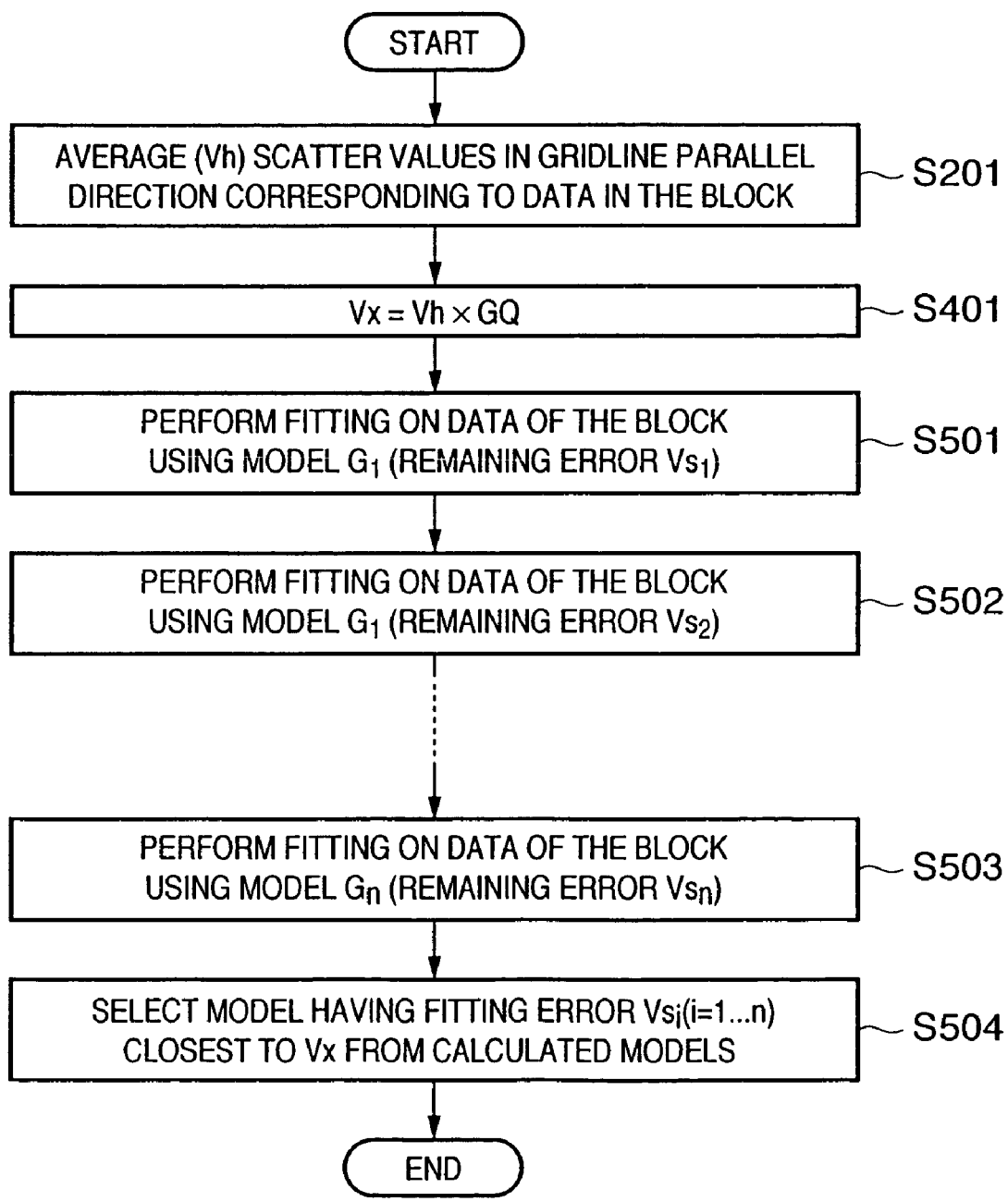
FIG. 9 is a flowchart describing a gridline prediction procedure according to a third embodiment.
Figure 10:
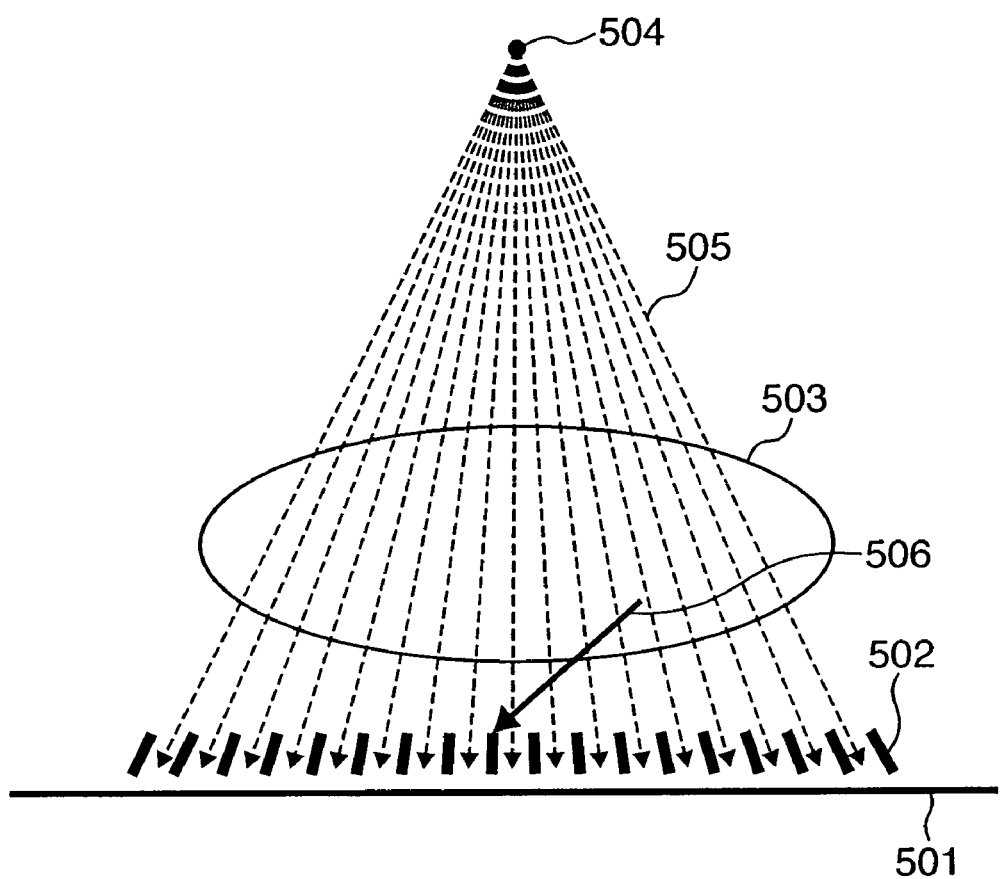
FIG. 10 is an explanatory view of scattered radiation removal using a grid.
Figure 11A:
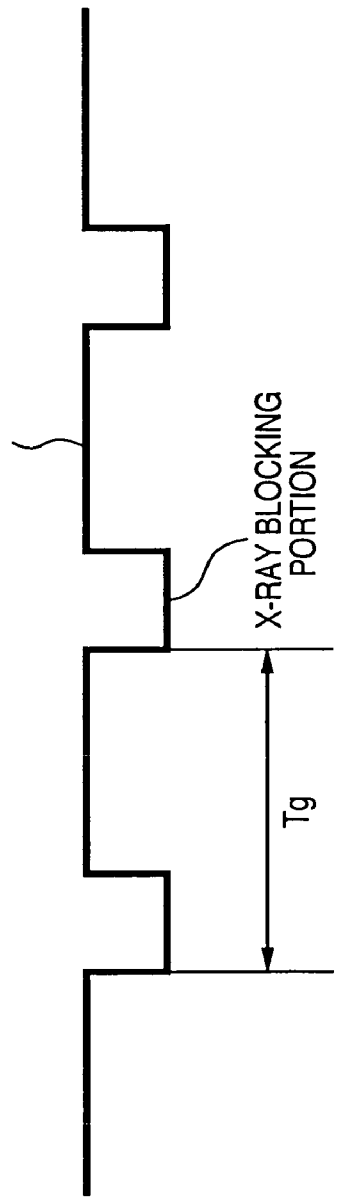
FIGS. 11A and 11B are explanatory views of gridlines on an image and their harmonics.
Figure 11B:
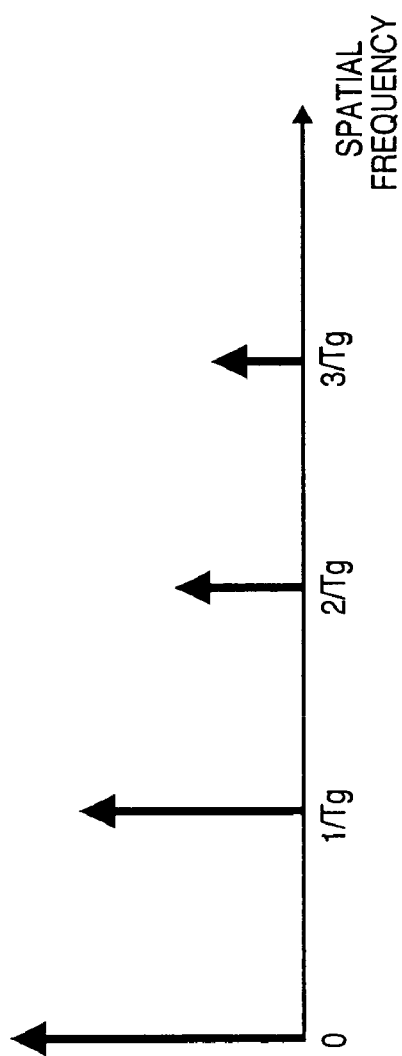

FIG. 9 is a flowchart describing fitting processing according to the third embodiment, where gridline prediction in the block is performed by fitting. This process replaces the process of the second embodiment shown in FIG. 8. As described in FIG. 8, the average scatter value Vh in the gridline parallel direction in the block is obtained (step S201), and the average scatter value is multiplied by GQ to obtain a target value Vx (step S401). In steps S501 to S503, fitting is performed on one data (one line) using the n number of models $G_1$ to $G_n$ to calculate respective remaining errors $Vs_1$ to $VS_n$. In step S504, a model having a remaining error closest to the target value Vx is selected as the gridlines, thereby realizing appropriate gridline prediction.

Note, although the third embodiment adopts the processing of the second embodiment, the average scatter value Vh employed in the first embodiment may be used as the target value. In this case, step S401 is omitted, and in step S504, a model having a remaining error closest to Vh is selected. Alternatively, a combined technique may be employed by performing fitting closest to Vx as similar to FIGS. 5 and 8 while changing the number of data points in each fitting of the respective models, and then by comparing the result of each model.

Fourth Embodiment

The GQ value described in the second embodiment is not only used in gridline removal, but also used in quality control of the grid itself. Although it is ideal that the GQ value is 1, if there is fixed noise other than the grid's fundamental frequency in the grid manufacturing process, a poor quality grid is produced. For instance, before the grid is actually used, the GQ value is obtained by the apparatus shown in FIG. 6 using the calculation method in FIG. 7. If the GQ value is 3 or more, or 0.8 or less, the grid is determined to be faulty, thus may be excluded. In other words, the GQ value can be utilized for sorting a faulty grid.

As has been described above, according to each of the above-described embodiments, by removing a harmonic component in addition to the fundamental wave component of the gridlines, it is possible to perform appropriate gridline removal even when an X-ray sensor having a high MTF is used. Furthermore, by setting an equivalent scatter value or a value multiplied by the grid quality value (GQ value) for the horizontal and vertical directions of the image, it is possible to perform proper gridline prediction.

Note that the gridline removal described in the first to third embodiments as well as the grid sorting in the fourth embodiment can be realized by a computer performing X-ray image data processing. Therefore, the object of the present invention can also be achieved by providing a storage medium storing program codes of a software realizing the functions of the above-described embodiments to a computer system or apparatus, reading the program codes, by a computer (CPU or MPU) of the computer system or apparatus, from the storage medium, then executing the program.

In this case, the program codes read from the storage medium realize the functions according to the embodiments, and the storage medium storing the program codes constitutes the invention.

The storage medium, such as a flexible disk, hard disk, an optical disk, a magneto-optical disk, CD-ROM, CD-R, a magnetic tape, a non-volatile type memory card, and ROM can be used for providing the program codes.

Furthermore, besides aforesaid functions according to the above embodiments are realized by executing the program codes which are read by a computer, the present invention includes a case where an OS (operating system) or the like working on the computer performs a part or the entire processes in accordance with designations of the program codes and realizes functions according to the above embodiments.

Furthermore, the present invention also includes a case where, after the program codes read from the storage medium are written in a function expansion card which is inserted into the computer or in a memory provided in a function expansion unit which is connected to the computer, a CPU or the like contained in the function expansion card or unit performs a part or the entire processes in accordance with designations of the program codes and realizes functions of the above embodiments.

According to the configuration of the present invention, it is possible to remove, in addition to the fundamental wave component of gridlines, a harmonic component of the gridlines from a radiographic image. By virtue of this, even in a case of using an X-ray sensor having a high MTF, it is possible to obtain a radiographic image which is less influenced by gridlines.

As many apparently widely different embodiments of the present invention can be made without departing from the spirit and scope thereof, it is to be understood that the invention is not limited to the specific embodiments thereof except as defined in the claims.

CLAIM OF PRIORITY

This application claims priority from Japanese Patent Application No. 2003-289157 filed on Aug. 7, 2003, which is hereby incorporated by reference herein.

What is claimed is:

1. A radiographic image processing method comprising:
   an obtaining step of obtaining a frequency of gridlines in a radiographic image;
   a generating step of generating gridline protection data corresponding to the frequency obtained in the obtaining step, by a computer, based on a first power of image signal component of the radiographic image in a first direction of traversing the gridlines and a second power of the image signal component of the radiographic image in a second direction parallel to the gridlines; and
   a removing step of removing the gridlines from the radiographic image based on the gridline prediction data generated in the generating step.

2. The method according to claim 1, further comprising:
   a forming step of forming a filter for extracting the image signal component which corresponds to the obtained frequency.

3. The method according to claim 1, wherein in the obtaining step, the frequency is obtained based on a frequency characteristic acquired by performing Fourier transformation on the radiographic image.

4. The method according to claim 1, wherein in the generating step, the gridline prediction data is generated so as to make equal the second power and a third power of an image signal component which is removed based on the gridline prediction data.

5. The method according to claim 4, wherein the generating step further comprises:
   a calculating step of calculating an average value and a scatter for each group of pixels of the image signal component, arranged in the second direction, with respect to a plurality of lines of pixels including a line of interest along the first direction; and
   an adjusting step of generating the gridline prediction data by adjusting a gridline model in a way that a first direction scatter and a second direction scatter becomes equal, the first direction scatter being a fitting error in the first direction in a case of fitting the gridline model using the average value and the second direction scatter being an average of scatters calculated in the calculating step.

6. The method according to claim 1, wherein in the generating step, the gridline prediction data is generated in units of predetermined number of pixels in the radiographic image.

7. The method according to claim 5, wherein in the adjusting step, the fitting is adjusted by thinning the average value used in the fitting processing.

8. The method according to claim 5, wherein in the adjusting step, the fitting is performed with respect to plural types of models prepared in advance, and a model having a smallest difference between the first direction scatter and the second direction scatter is adopted.

9. The method according to claim 1, wherein the generating step employs the radiographic image except for a portion having a signal amplitude value larger than a predetermined value and/or a portion having a phase variation value larger than a predetermined value, and
   the gridline prediction data is generated by interpolating the removed portion based on a result of the fitting processing.

10. The method according to claim 1, further comprising an acquisition step of acquiring a power ratio of the power of the image signal component in the first direction to a power of the image signal component in the second direction based on a gridline image obtained by radiographing the grid only,
   wherein in the generating step, the gridline prediction data is generated in a way that a difference between the power of the image signal component in the first direction and a value, obtained by operating the power of the image signal component in the second direction by the power ratio, becomes equal.

11. The method according to claim 10, wherein in the acquisition step, a power spectrum is calculated with respect to each of the first and second directions of the gridline image, a sum of the power spectrum except for a portion of the frequency of the gridlines obtained in the obtaining step is obtained for each direction, and a ratio of the sum of the power spectrum in the first direction to the sum of the power spectrum in the second direction is calculated as the power ratio.

12. An image processing apparatus comprising: an obtaining means for obtaining a frequency of gridlines in a radiographic image;
a generating unit configured to generate gridline prediction data corresponding to the frequency obtained by the obtaining unit, based on a first power of image signal component of the radiographic image in a first direction of traversing the gridlines and a second power of the image signal component of the radiographic image in a second direction parallel to the gridlines; and
a removing unit configured to remove the gridlines from the radiographic image based on the gridline prediction data generated by the generating unit.

13. A computer readable medium storing a control program which causes a computer to execute the radiographic image processing method, the method comprising:
an obtaining step of obtaining a frequency of gridlines in a radiographic image;
a generating step of generating gridline prediction data corresponding to the frequency obtained in the obtaining step, by a computer, based on a first power of image signal component of the radiographic image in a first direction of traversing the gridlines and a second power of the image signal component of the radiographic image in a second direction parallel to the gridlines;
a removing step of removing the gridlines from the radiographic image based on the gridline prediction data generated in the generating step.

14. The method according to claim 1, wherein the frequency of gridlines obtained in the obtaining step includes at least one of a fundamental frequency and a harmonic frequency.

15. The apparatus according to claim 12, wherein the frequency of gridlines obtained by the obtaining means includes at least one of a fundamental frequency and a harmonic frequency.

16. A radiographic image processing method comprising:
an obtaining step of obtaining from a radiographic image, a fundamental frequency and at least one harmonic frequency consisting a gridline;
a generating step of generating gridline prediction data corresponding to the fundamental frequency and the at least one harmonic frequency obtained in the obtaining step, by a computer, in a way that a power of image signal component of the radiographic image in a first direction of traversing the gridlines and a power of the image signal component of the radiographic image in a second direction parallel to the gridlines become equal;
a removing step of removing gridlines from the radiographic image based on the gridline prediction data generated in the generating step.

17. A radiographic image processing apparatus comprising:
an obtaining means for obtaining from a radiographic image, a fundamental frequency and at least one harmonic frequency consisting a gridline;
a generating unit configured to generate gridline prediction data corresponding to the fundamental frequency and the at least one harmonic frequency obtained by the obtaining unit, in a way that a power of image signal component of the radiographic image in a first direction of traversing the gridlines and a power of the image signal component of the radiographic image in a second direction parallel to the gridlines become equal;
a removing unit configured to remove gridlines from the radiographic image based on the gridline prediction data generated by the generating unit.

* * * * *